United States Patent [19]

Gante et al.

[11] 4,060,633
[45] Nov. 29, 1977

[54] PHENYLALKANOL NITRILES

[75] Inventors: Joachim Gante; Hans-Adolf Kurmeier; Dieter Orth; Erich Schacht; Albrecht Wild, all of Darmstadt, Germany

[73] Assignee: Merck Patent Gesellschaft mit beschrankter Haftung, Darmstadt, Germany

[21] Appl. No.: 681,175

[22] Filed: Apr. 28, 1976

[30] Foreign Application Priority Data

May 2, 1975   Germany .............................. 2519719

[51] Int. Cl.$^2$ ................... A61K 31/275; C07C 121/75
[52] U.S. Cl. .................................... 424/304; 260/192;
260/456 R; 260/456 P; 260/462 R; 260/465 E;
260/465 F; 260/571; 260/592; 260/611 A;
260/612 R; 260/613 R; 260/618 R; 260/618 D;
424/341; 424/343; 560/255; 560/107
[58] Field of Search ..................... 260/465 F; 424/304
[56] References Cited

U.S. PATENT DOCUMENTS 3,462,483   8/1969   Petrow et al. ................... 260/465 X Primary Examiner—Dolph H. Torrence Attorney, Agent, or Firm—Millen & White

[57] ABSTRACT

Phenylalkanols of the formula

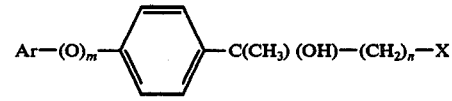

wherein Ar is phenyl or phenyl monosubstituted or disubstituted by F, Cl, Br and/or $CH_3$; X is F, Cl, Br or CN; $m$ is 0 or 1; and $n$ 2 or 3; possess antiinflammatory activity and can be produced by treating a compound of formula

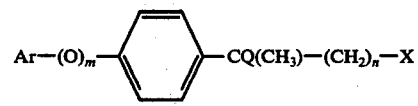

wherein Q is a functionally modified hydroxy group and Ar, X, $m$ and $n$ have the values given above, with a solvolyzing agent.

19 Claims, No Drawings

PHENYLALKANOL NITRILES

BACKGROUND OF THE INVENTION

This invention relates to novel phenylalkanols.

SUMMARY OF THE INVENTION

In a composition aspect, this invention relates to novel phenylalkanols of general Formula I

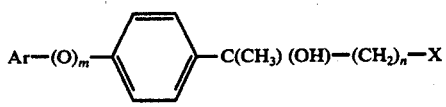

wherein Ar is phenyl or phenyl monosubstituted or disubstituted by F, Cl, Br and/or $CH_3$, X is F, Cl, Br or CN, m is 0 or 1 and n is 2 or 3.

In another composition aspect, this invention relates to pharmaceutical compositions comprising a novel phenylalkanol of this invention. In process aspects, this invention relates to processes for the production and use thereof.

In the compounds of Formula I, Ar is preferably unsubstituted phenyl or monosubstituted phenyl, especially monosubstituted phenyl in which the substituent is preferably in the p-position, but can also be in the o-position or m-position. In the case of disubstituted phenyl, the substituents are preferably in the 2,4-position but they can also be in the 2,3-, 2,5-, 2,6-, 3,4- or 3,5-position. The substituents can be identical or different. Ar is preferably phenyl, o-, m- and especially p-fluorophenyl, o-,m- and especially p-chlorophenyl, o-, m- or p-bromophenyl, o-, m- or p-tolyl, 2,3-, 2,5-, 2,6-, 3,4-, 3,5- or, in particular, 2,4-difluorophenyl, 2,3-, 2,5-, 2,6-, 3,4-, 3,5- and especially, 2,4-dichlorophenyl, chloro-fluorophenyl, e.g., 2-chloro-3-, -4-, -5- or -6-fluorophenyl, 3-chloro-2-, -4- or -5-fluorophenyl, 4-chloro-2- or -3-fluorophenyl or 5-chloro-2-fluorophenyl, dibromophenyl, e.g., 2,4-dibromophenyl, bromo-fluoro-phenyl, e.g., as 2-bromo-4-fluoro-phenyl or 4-bromo-2-fluoro-phenyl, bromo-chloro-phenyl, e.g., 2-bromo-4-chloro-phenyl or 4-bromo-2-chlorophenyl, dimethylphenyl, e.g., 2,3-, 2,4-, 2,5-, 2,6-, 3,4- or 3,5- dimethylphenyl, fluoro-methylphenyl, such as 2-fluoro-4-methylphenyl or 4-fluoro-2-methylphenyl, chloro-methyl-phenyl, e.g., 2-chloro-4-methylphenyl or 4-chloro-2-methylphenyl, or bromo-methyl-phenyl, e.g., 2-bromo-4-methylphenyl or 4-bromo-2-methylphenyl.

In the preferred compounds, X is F, Cl or CN.

In the preferred compounds m is 0. Accordingly, the group $Ar-(O)_m-(p-C_6H_4)$- is preferably 4-biphenylyl, 2'- or 4'-fluoro-4-biphenylyl, 2'- or 4'-chloro-4-biphenylyl, 2', 4'-difluoro-4-biphenylyl or 2'-methyl-4'-fluoro-4-biphenylyl. Other examples are p-phenoxyphenyl, p-4-fluorophenoxyphenyl and p-4-chlorophenoxyphenyl. In the preferred compounds, n is 2.

Accordingly, the invention relates in particular to those compounds of Formula I in which at least one of Ar, X, m and n have one of the preferred values given above.

Preferred groups of compounds are those which otherwise correspond to Formula I but wherein:

Ia. Ar is phenyl, fluorophenyl, chlorophenyl, tolyl, difluorophenyl or fluoromethylphenyl;

Ib. Ar is phenyl, o- or p-fluorophenyl, p-chlorophenyl, 2,4-difluorophenyl or 2-methyl-4-fluorophenyl;

Ic. Ar is phenyl, o- or p-fluorophenyl, p-chlorophenyl, 2,4-difluorophenyl or 2-methyl-4-fluorophenyl, X is F, Cl or CN and m is 1;

Id. Ar is phenyl, o- or p-fluorophenyl, p-chlorophenyl, 2,4-difluorophenyl or 2-methyl-4-fluorophenyl, X is F or Cl and m is 0;

Ie. Ar is phenyl, o- or p-fluorophenyl, p-chlorophenyl, 2,4-difluorophenyl or 2-methyl-4-fluorophenyl and n is 2;

If. Ar is phenyl, o- or p-fluorophenyl, 2,4-difluorophenyl or 2-methyl-4-fluorophenyl, X is Cl, m is 0 and n is 2; and Ig. Ar is p-fluorophenyl and m is 0.

In process aspects, this invention relates to a process for the preparation of the compounds of Formula I, wherein:

a. a compound of the general Formula II

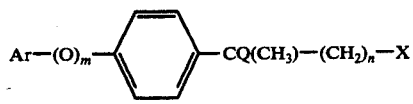

wherein Q is a functionally modified hydroxyl group and Ar, X, m and n have the values given above, is treated with a solvolyzing agent; or b. an amino compound of the general Formula III

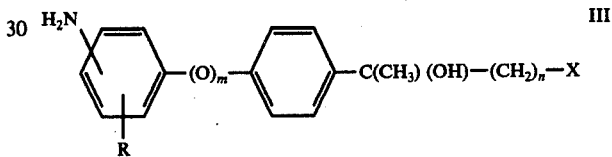

wherein R is H, F, Cl, Br, $CH_3$ or $NH_2$ and X, m and n have the values given above, is diazotized and the resulting diazonium salt is subsequently treated with a halogenating agent; or c. a compound of the general Formula IV

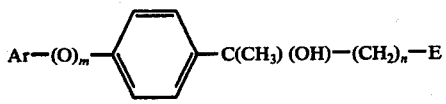

wherein E is a free or functionally modified hydroxyl group, is reacted with an inorganic halide or cyanide.

Optionally, in a thus-produced compound of Formula I, X is converted into another value given above for X by treatment with an inorganic halide or cyanide, and/or one or two chlorine or bromine atoms are introduced into the Ar radical by treatment with a chlorinating or brominating agent.

For simplicity, hereinafter

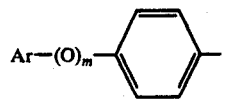

is designated "Y".

In other respects, the preparation of the compounds of Formula I is carried out in accordance with methods which are in themselves known, such as described in the literature (for example, in the standard works, such as Houben-Weyl, Methoden der Organischen Chemie (Methods of Organic Chemistry), Georg-Thieme-Verlag, Stuttgart and Organic Reactions, John Wiley & Sons, Inc., New York) and in particular under the reaction conditions which are known and suitable for the reactions described. It is also possible to use variants which are in themselves known and are not mentioned in more detail here.

Some of the starting compounds for the preparation of the compounds of Formula I are known. Those which are new can be prepared according to processes which are in themselves known. If desired, the starting compounds can also be formed in situ in such a way that they are not isolated from the reaction mixture but are immediately reacted further to give a compound of Formula I.

Preferably, the compounds of Formula I are prepared by solvolysis, especially hydrolysis, of corresponding functionally modified compounds of Formula II. In the latter compounds, the radical Q is a functionally modified hydroxyl group, preferably a metal alcoholate, especially a magnesium alcoholate or lithium alcoholate, such as are formed as reaction products in Grignard reactions or reactions with organo-lithium compounds. Such alcoholates of the formula $Y-C(CH_3)(OM)-(CH_2)_n-X$ (IIa) wherein M is one equivalent of a metal atom, preferably Li, or the group MgHal and Hal is Cl, Br or I and X, Y and $n$ have the values given above, are preferably prepared in situ. They are obtainable, for example, by reacting ketones of the formula $Y-CO-(CH_2)_n-X$ with organometallic compounds of the formula $CH_3-M$ under the conditions conventional for a Grignard synthesis, preferably in an inert solvent, e.g., diethyl ether or tetrahydrofuran (THF), or in a solvent mixture at a temperature of 0° to 70°, and also by reacting ketones of the formula $Y-CO-CH_3$ with organometallic compounds of the formula $M-(CH_2)_n-X$ or by reacting ketones of the formula $CH_3-CO-(CH_2)_n-X$ with organometallic compounds of the formula $Y-M$, under the same conditions. Ketones of the formula $Y-CO-(CH_2)_n-X$ can be prepared, for example, by Friedel-Crafts acylation of compounds of the formula $Y-H$ with acid chlorides of the formula $Cl-CO-(CH_2)_n-X$ in the presence of $AlCl_3$. The ketones of the formula $Y-CO-CH_3$ can be prepared analogously from $Y-H$ and acetyl chloride and the organometallic compounds $Y-M$ can be prepared by halogenating $Y-H$ and reacting the resulting halogeno compounds of the formula $Y-Hal$ with magnesium or lithium.

In these starting compounds, Q can also be present in the form of an ester, for example, as a carboxylic acid ester in which the carboxylic acid radical preferably contains up to 7 carbon atoms (for example, acetyl or benzoyl) or as an alkylsulfonic acid ester or arylsulfonic acid esters (wherein the alkyl preferably contains 1 to 6 carbon atoms and the aryl preferably contains 6 to 10 carbon atoms), or as an ether, for example, an alkyl ether (wherein the alkyl group preferably contains up to 6 carbon atoms), an aryl ether (wherein the aryl group preferably contains 6 to 10 carbon atoms) or an aralkyl ether (wherein the aralkyl group preferably has 7 to 11 carbon atoms). The boric acid esters which are formed as intermediate products in oxidative hydroborination can also be employed. Q can also be Cl, Br or I, i.e., a hydrogen halide acid ester group.

The solvolysis of the compounds of Formula II can be carried out in an acid, neutral or alkaline medium at temperatures of about −20° to 300°. Acid catalysts used for the solvolysis are preferably hydrochloric acid, sulfuric acid or acetic acid as well as acetic salts, e.g., ammonium chloride. Basic catalysts which can be used include sodium hydroxide, potassium hydroxide, calcium hydroxide, sodium carbonate and potassium carbonate. The solvents are preferably water, lower alcohols, e.g., methanol or ethanol, ethers, e.g., THF or dioxane, amides, e.g., dimethylformamide (DMF), nitriles, e.g., acetonitrile, sulfones, e.g., tetramethylenesulfone, and mixtures of these solvents, especially mixtures which contain water.

The metal alcoholates of Formula IIa, which are preferred as starting materials, are preferably not isolated but instead, after their formation, are hydrolyzed in situ with dilute acids, for example, sulfuric acid or hydrochloric acid, or with an aqueous solution of ammonium chloride, preferably at temperatures from 0° to 30°.

Halogen-containing compounds of Formula I can also be obtained from the corresponding amino compounds of Formula III by first diazotizing the latter, e.g., with salts or esters of nitrous acid (e.g., $NaNO_2$ or n-butyl nitrite) in aqueous hydrochloric acid at temperatures of about −20° to +10° and subsequently converting the resulting diazonium salt into the halogen compound. Fluorine compounds (corresponding to III but having an F atom instead of the amino group or groups) are preferably obtained by reacting the diazonium salt with $HBF_4$ to give the diazonium tetrafluoborate and subsequently decomposing the latter by heating at about 100° to 200° in the absence or presence of an inert solvent, e.g., toluene, xylene or dioxane. A decomposition at room temperature in an aqueous medium in the presence of copper powder is also possible. If the diazotization is carried out with $NaNO_2$ in anhydrous hydrofluoric acid, the desired fluorine compound is obtained direclty on subsequent warming. The diazonium group is exchanged by chlorine or bromine, preferably in a hot aqueous solution in the presence of $Cu_2Cl_2$ or $Cu_2Br_2$. The starting compounds of Formula III are obtainable, for example, by reducing corresponding nitro compounds (corresponding to III but having a $NO_2$ group instead of the amino group or groups) and these in turn can be prepared by nitrating the corresponding unsubstituted compounds.

The phenylalkanols of Formula I can also be obtained by reacting a compound of Formula IV (which differs from I) with an inorganic halide or cyanide.

In the compounds of Formula IV, E is preferably a free hydroxyl group or a hydroxyl group which is functionally modified in the form of a reactive ester, e.g., alkylsulfonic acid esters or arylsulfonic acid esters wherein the alkyl group preferably contains 1 to 6 carbon atoms and the aryl groups preferably contains 6 to 10 carbon atoms, e.g., the methanesulfonates, benzenesulfonates, p-toluenesulfonates and 1- or 2-naphthalenesulfonates. Examples of suitable inorganic halides are, in particular, the free hydrogen halide acids HF, HCl or HBr, the metal salts derived therefrom, especially the alkali metal salts or alkaline earth metal salts, e.g., LiF, LiCl, LiBr, NaF, NaCl, NaBr, KF, KCl, KBr, $MgF_2$, $MgCl_2$, $MgBr_2$, $CaF_2$, $CaCl_2$, and $CaBr_2$, and also heavy metal halides, e.g., $ZnF_2$, as well as acid halides, e.g., $SOCl_2$, $PCl_3$, $PBr_3$, $POCl_3$ and $SbF_3$, and mixed halogen compounds, e.g., $BrF_3$. Examples of suitable inorganic cyanides are, in particular, the alkali metal cyanides, e.g., as NaCN or KCN, as well as heavy metal cyanides, e.g., $Cu_2(CN)_2$.

The reaction of a compound of Formula IV with an inorganic halide or cyanide is carried out in the absence or presence of one or more additional inert solvents, preferably at a temperature of about $-20°$ to $+200°$, especially 20° to 150°. Examples of suitable inert solvents are hydrocarbons, e.g., benzene, halogenated hydrocarbons, e.g., dichloromethane, chloroform or trichloroethylene, ethers, e.g., diethyl ether, THF or dioxane, amides, e.g., DMF, sulfoxides, e.g., dimethylsulfoxide, tertiary amines, e.g., triethylamine or pyridine. If one of the salts mentioned is used for the reaction with the compound of Formula IV, it is also possible to use an alcohol, e.g., methanol or ethanol, or a glycol, e.g., ethylene glycol or diethylene glycol, as the solvent. The starting compounds of Formula IV are obtainable, for example, by reacting a ketone of the formula $Y-CO-CH_3$ with ethyl bromoacetate or 3-bromopropionic acid ethyl ester in the presence of zinc to give the corresponding hydroxy-ester of the formula $Y-C(CH_3)(OH)-(CH_2)_{n-1}-COOC_2H_5$ and subsequently reducing this compound to a diol of the formula $Y-C(CH_3)(OH)-(CH_2)_n-OH$. If desired, the primary hydroxyl group can be selectively functionally modified, e.g., esterified.

If desired, it is possible, in a resulting compound of Formula I, to convert the X radical into another value for X by treatment with an inorganic halide or cyanide. In particular, it is possible to prepare, from chlorine compounds of Formula I ($X = Cl$), the corresponding fluorine compounds of Formula I ($X = F$) by reaction with fluorides, especially alkali metal fluorides, and the corresponding cyano compounds of Formula I ($X = CN$) by reaction with cyanides, especially alkali metal cyanides. In other respects it is advantageous in these reactions to employ the conditions described above for the preparation of compounds of Formula I from compounds of Formula IV.

It is also possible, in a resulting compound of Formula I in which the Ar radical is at most monosubstituted, to introduce one or two chlorine or bromine atoms by halogenation in accordance with methods described in the literature, for example, by direct reaction, preferably at temperatures of $-30°$ to 100°, with elementary chlorine or bromine in an inert solvent, e.g., ether, carbon tetrachloride, or acetic acid, it being possible for catalysts, e.g., iron filings, iodine or $AlCl_3$, to be present.

The compounds of Formula I contain a center of asymmetry and are usually in the racemic form. The racemates can be resolved into their optical antipodes employing known mechanical or chemical methods. Optically active compounds of Formula I are also obtainable by employing optically active starting compounds, e.g., those of Formula III or IV.

The compounds of Formula I possess valuable pharmacological properties and are well tolerated. In particular, they possess antiphlogistic activity which can be demonstrated on rats, for example in the adjuvant-arthritis test by the method of Newbould (Brit. J. Pharmacol., volume 21 (1963), pages 127–136). Analgesic and antipyretic effects also are exhibited and can be demonstrated by methods conventionally employed for this purpose. They also exhibit serum cholesterol level lowering activity (which can be demonstrated by the method of Levine et al., Automation in Analytical Chemistry, Technicon Symposium 1967, Mediad, New York, pages 25 – 28), serum triglyceride level lowering activity (which can be demonstrated by the method of Noble and Campbell, Clin. Chem. volume 16 (1970), pages 166–170), and uric acid level lowering activity. They also activate the liver enzymes and inhibit the aggregation of thrombocytes.

The compounds of Formula I can therefore be used as medicaments in human medicine and veterinary medicine. They are also useful as intermediate products for the preparation of other medicaments. Thus, for example, the halogeno alcohols of Formula I ($X = Cl$ or $Br$) can be reacted with ammonia or primary or secondary amines to give the corresponding amino compounds, which also possess valuable pharmacological actions, such as antiphlogistic activity.

The compounds of Formula I can be used, preferably mixed with solid, liquid and/or semi-liquid medicinal excipients, as medicaments in human medicine or veterinary medicine. Excipients which can be used include both organic or inorganic substances which are suitable for enteral or parenteral administration or topical application and which do not react with the new compounds, for example, water, vegetable oils, benzyl alcohols, polyethylene glycols, gelatine, lactose, starch, magnesium stearate, talc and white petroleum jelly. Suitable formulations for enteral administration are, for example, tablets, dragees, capsules, syrups, elixirs or suppositories. Formulations suitable for parenteral administration are, in particular, solutions, preferably oily or aqueous solutions, and also suspensions, emulsions or implants. Those useful for topical application include ointments, creams or powders. The new compounds can also be lyophilized and the resulting lyophilizates can be used, for example, to prepare injection formulations. These formulations can be sterilized and/or contain auxiliaries, e.g., lubricants, preservatives, stabilizers and/or wetting agents, emulsifiers, salts for regulating the osmotic pressure, buffer substances, dyestuffs, flavorings, and/or aromatic substances. They can, if desired, also contain one or more further active compounds, e.g., vitamins.

As a rule, the compounds of the invention are administered analogously to known antiphlogistic agents which are available commercially, preferably in dosages of about 10 to 1,000 mg., especially 30 to 300 mg. per dosage unit. The daily dose is preferably about 0.2 to 20 mg./kg. of body weight. Oral administration is preferred.

Each of the compounds of Formula I mentioned in the examples which follow is particularly suitable for the preparation of pharmaceutical formulations.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the examples which follow "customary working up" means: water is added if necessary, the mixture is extracted with an organic solvent, such as benzene, chloroform or dichloromethane, the phases are separated, the organic phase is dried over sodium sulfate and filtered, the filtrate is evaporated and the product is purified by chromatography and/or crystallization. Temperatures are in degrees Celsius.

EXAMPLE 1

A Grignard solution is prepared from 3.65 g. of magnesium filings, 9.5 ml. of methyl iodide and 120 ml. of ether. A solution of 26.25 g. of 4-(2-chloropropionyl)-4'-fluoro-biphenyl (which can be obtained from 4'-fluoro-biphenyl and 2-chloro-propionyl chloride in the presence of AlCl$_3$) in a mixture of 350 ml. of ether and 20 ml. of THF is added dropwise to this solution, while stirring. After stirring for a further 1 hour at 20°, the magnesium alcoholate of the formula p-F-C$_6$H$_4$-p-C$_6$H$_4$-C(OMgI) (CH$_3$)-(CH$_2$)$_2$-Cl, which has formed in situ, is hydrolyzed by adding 200 ml. of 2 N hydrochloric acid dropwise while stirring. The customary working up gives 1-chloro-3-(4'-fluoro-4-biphenylyl)-butan-3-ol, m.p. 78° – 79°.

EXAMPLES 2 – 32

Analogously to Example 1,
1-Chloro-3-(4-biphenylyl)-butan-3-ol, m.p. 68°–70°;
1-Chloro-3-(2'-fluoro-4-biphenylyl)-butan-3-ol, n$_D^{20}$ 1.5842;
1-Chloro-3-(3'-fluoro-4-biphenylyl)-butan-3-ol;
1-Chloro-3-(2'-chloro-4-biphenylyl-butan-3-ol;
1-Chloro-3-(3'-chloro-4-biphenylyl)-butan-3-ol;
1-Chloro-3-(4'-chloro-4-biphenylyl)-butan-3-ol, m.p. 98° – 100°;
1-Chloro-3-(2'-bromo-4-biphenylyl)-butan-3-ol;
1-Chloro-3-(3'-bromo-4-biphenylyl)-butan-3-ol;
1-Chloro-3-(4'-bromo-4-biphenylyl)-butan-3-ol;
1-Chloro-3-(2'-methyl-4-biphenylyl)-butan-3-ol;
1-Chloro-3-(3'-methyl-4-biphenylyl)-butan-3-ol;
1-Chloro-3-(4'-methyl-4-biphenylyl)-butan-3-ol;
1-Chloro-3-(2',4'-difluoro-4-biphenylyl)-butan-3-ol;
1-Chloro-3-(2'-methyl-4'-fluoro-4-biphenylyl)-butan-3-ol, n$_D^{20}$ 1.5741;
1-Chloro-3-(2',4'-biphenylyl)-butan-3-ol;
1-Chloro-3-(4-phenoxyphenyl)-butan-3-ol;
1-Chloro-3-(4-o-fluorophenoxy-phenyl)-butan-3-ol;
1-Chloro-3-(4-m-fluorophenoxy-phenyl)-butan-3-ol;
1-Chloro-3-(4p-fluorophenoxy-phenyl)-butan-3-ol;
1-Chloro-3-(4-o-chlorophenoxy-phenyl)-butan-3-ol;
1-Chloro-3-(4-m-chlorophenoxy-phenyl)-butan-3-ol;
1-Chloro-3-(4-p-chlorophenoxy-phenyl)-butan-3-ol;
1-Chloro-3-(4-o-bromophenoxy-phenyl)-butan-3-ol;
1-Chloro-3-(4-m-bromophenoxy-phenyl)-butan-3-ol;
1-Chloro-3-(4-p-bromophenoxy-phenyl)-butan-3-ol;
1-Chloro-3-(4-o-tolyloxy-phenyl)-butan-3-ol;
1-Chloro-3-(4-m-tolyloxy-phenyl)-butan-3-ol;
1-Chloro-3-(4-p-tolyloxy-phenyl)-butan-3-ol;
1-Chloro-3-[4-(2,4-difluorophenoxy)-phenyl]-butan-3-ol;
1-Chloro-3-[4-(2-methyl-4-fluorophenoxy)-phenyl]-butan-3-ol; and
1-Chloro-3-[4-(2,4-dichlorophenoxy)-phenyl]-butan-3-ol; are obtained from 4-(2-chloropropionyl)-biphenyl, 4-(2-chloropropionyl)-2'-fluoro-biphenyl, 4-(2-chloro-propionyl)-3'-fluoro-biphenyl, 4-(2-chloro-propionyl)-2'-, -3'- or 4'-chloro-biphenyl, 4-(2-chloropropionyl)-2'-, -3'- or 4'-bromobiphenyl, 4-(2-chloropropionyl)-2'-, -3'- or –4'-methylbiphenyl, 4-(2-chloropropionyl)-2',4'-difluoro-biphenyl, 4-(2-chloropropionyl)-2'-methyl-4'-fluoro-biphenyl, 4-(2-chloropropionyl)-2',4'-dichloro-biphenyl, 4-(2-chloropropionyl)-diphenyl ether, 4-(2-chloropropionyl)-2'-, -3'- or -4'-fluorodiphenyl ether, 4-(2-chloro-propionyl)-2'-, -3'- or -4'-chlorodiphenyl ether, 4-(2-chloropropionyl)-2'-, -3'- or -4'-bromodiphenyl ether, 4-(2-chloropropionyl)-2'-, -3'- or -4'-methyl-diphenyl ether, 4-(2-chloropropionyl)-2',4'-difluoro-diphenyl ether, 4-(2-chloropropionyl)-2'-methyl-4'-fluoro-diphenyl ether and 4-(2-chloropropionyl)-2',4'-dichloro-diphenyl ether, respectively, and CH$_3$MgI.

EXAMPLES 33 – 64

Analogously to Example 1,
1-Bromo-3-(4-biphenylyl)-butan-3-ol;
1-Bromo-3-(2'-fluoro-4-biphenylyl)-butan-3-ol;
1-Bromo-3-(3'-fluoro-4-biphenylyl)-butan-3-ol;
1-Bromo-3-(4'-fluoro-4-biphenylyl)-butan-3-ol, m.p. 72°–74°;
1-Bromo-3-(2'-chloro-4-biphenylyl)-butan-3-ol;
1-Bromo-3-(3'-chloro-4-biphenylyl)-butan-3-ol;
1-Bromo-3-(4'-chloro-4-biphenylyl)-butan-3-ol;
1-Bromo-3-(2'-bromo-4-biphenylyl)-butan-3-ol;
1-Bromo-3-(3'-bromo-4-biphenylyl)-butan-3-ol;
1-Bromo-3-(4'-bromo-4-biphenylyl)-butan-3-ol;
1-Bromo-3-(2'-methyl-4-biphenylyl)-butan-3-ol;
1-Bromo-3-(3'-methyl-4-biphenylyl)-butan-3-ol;
1-Bromo-3-(4'-methyl-4-biphenylyl)-butan-3-ol;
1-Bromo-3-(2',4'-difluoro-4-biphenylyl)-butan-3-ol;
1-Bromo-3-(2'-methyl-4'-fluoro-4-biphenylyl)-butan-3-ol;
1-Bromo-3-(2',4'-dichloro-4-biphenylyl)-butan-3-ol;
1-Bromo-3-(4-phenoxyphenyl)-butan-3-ol;
1-Bromo-3-(4-o-fluorophenoxy-phenyl)-butan-3-ol;
1-Bromo-3-(4-m-fluorophenoxy-phenyl)-butan-3-ol;
1-Bromo-3-(4-p-fluorophenoxy-phenyl)-butan-3-ol;
1-Bromo-3-(4-o-chlorophenoxy-phenyl)-butan-3-ol;
1-Bromo-3-(4-m-chlorophenoxy-phenyl)-butan-3-ol;
1-Bromo-3-(4-p-chlorophenoxy-phenyl)-butan-3-ol;
1-Bromo-3-(4-o-bromophenoxy-phenyl)-butan-3-ol;
1-Bromo-3-(4m-bromophenoxy-phenyl)-butan-3-ol;
1-Bromo-3-(4-p-bromophenoxy-phenyl)-butan-3-ol;
1-Bromo-3-(4-o-tolyloxy-phenyl)-butan-3-ol;
1-Bromo-3-(4-m-tolyloxy-phenyl)-butan-3-ol;
1-Bromo-3-(4-p-tolyloxy-phenyl)-butan-3-ol;
1-Chloro-3-[4-(2,4-difluorophenoxy)-phenyl]-butan-3-ol;
1-Chloro-3-[4-(2-methyl-4-fluorophenoxy)-phenyl]-butan-3-ol; and
1-Chloro-3-(4-2,4-dichlorophenoxy)-phenyl]-butan-3-ol are obtained from the corresponding 4-(2-bromopropionyl)-biphenyls, 4-(2-chloropropionyl)- or 4-(2-bromopropionyl)-diphenyl ethers and CH$_3$MgI.

EXAMPLES 65 – 96

Analogously to Example 1,
1-Chloro-4-(4-biphenylyl)-pentan-4-ol;
1-Chloro-4-(2'-fluoro-4-biphenylyl)-pentan-4-ol;
1-Chloro-4-(3'-fluoro-4-biphenylyl)-pentan-4-ol;
1-Chloro-4-(4'-fluoro-4-biphenylyl)-pentan-4-ol, m.p. 70° – 72°;
1-Chloro-4-(2'-chloro-4-biphenylyl)-pentan-4-ol;
1-Chloro-4-(3'-chloro-4-biphenylyl)-pentan-4-ol;
1-Chloro-4-(4'-chloro-4-biphenylyl)-pentan-4-ol;
1-Chloro-4-(2'-bromo-4-biphenylyl)-pentan-4-ol;
1-Chloro-4-(3'-bromo-4-biphenylyl)-pentan-4-ol;
1-Chloro-4-(4'-bromo-4-biphenylyl)-pentan-4-ol;
1-Chloro-4-(2'-methyl-4-biphenylyl)-pentan-4-ol;
1-Chloro-4-(3'-methyl-4-biphenylyl)-pentan-4-ol;
1-Chloro-4-(4'-methyl-4-biphenylyl)-pentan-4-ol;
1-Chloro-4-(2',4'-difluoro-4-biphenylyl)-pentan-4-ol;
1-Chloro-4-(2'-methyl-4'-fluoro-4-biphenylyl)-pentan-4-ol;
1-Chloro-4-(2',4'-dichloro-4-biphenylyl)-pentan-4-ol;
1-Chloro-4-(4-phenoxyphenyl)-pentan-4-ol;
1-Chloro-4-(4-o-fluorophenoxy-phenyl)-pentan-4-ol;
1-Chloro-4-(4-m-fluorophenoxy-phenyl)-pentan-4-ol;
1-Chloro-4-(4-p-fluorophenoxy-phenyl)-pentan-4-ol;
1-Chloro-4-(4-o-chlorophenoxy-phenyl)-pentan-4-ol;

1-Chloro-4-(4-m-chlorophenoxy-phenyl)-pentan-4-ol;
1-Chloro-4-(4-p-chlorophenoxy-phenyl)-pentan-4-ol;
1-Chloro-4-(4-o-bromophenoxy-phenyl)-pentan-4-ol;
1-Chloro-4-(4-m-bromophenoxy-phenyl)-pentan-4-ol;
1-Chloro-4-(4-p-bromophenoxy-phenyl)-pentan-4-ol;
1-Chloro-4-(4-o-tolyloxy-phenyl)-pentan-4-ol;
1-Chloro-4-(4-m-tolyloxy-phenyl)-pentan-4-ol;
1-Chloro-4-(4-p-tolyloxy-phenyl)-pentan-4-ol;
1-Chloro-4-[4(4-(2,4-difluorophenoxy)-phenyl]-pentan-4-ol;
1-Chloro-4-[4-(2-methyl-4-fluorophenoxy)-phenyl]-pentan-4-ol; and
1-Chloro-4-[4-(2,4-dichlorophenoxy)-phenyl]-pentan-4-ol, are obtained from the corresponding 4-(3-chlorobutyryl)-biphenyls or 4-(3-chlorobutyryl)-diphenyl ethers and $CH_3MgI$.

EXAMPLE 97

A mixture of 27.9 g. of 1-chloro-3-(4'-fluoro-4-biphenylyl)-butan-3-ol, 8.7 g. of KF, 10 ml. of ethylene glycol and 5 ml. of diethylene glycol is heated to 140° – 150° for 8 hours. It is cooled and worked up in the customary manner and gives 1-fluoro-3-(4'-fluoro-4-biphenylyl)-butan-3-ol, m.p. 90° – 92°.

EXAMPLES 98 – 128

Analogously to Example 97,
1-Fluoro-3-(4-biphenylyl)-butan-3-ol;
1-Fluoro-3-(2'-fluoro-4-biphenylyl)-butan-3-ol;
1-Fluoro-3-(3'-fluoro-4-biphenylyl)-butan-3-ol;
1-Fluoro-3-(2'-chloro-4-biphenylyl)-butan-3-ol;
1-Fluoro-3-(3'-chloro-4-biphenylyl)-butan-3-ol;
1-Fluoro-3-(4'-chloro-4-biphenylyl)-butan-3-ol;
1-Fluoro-3-(2'-bromo-4-biphenylyl)-butan-3-ol;
1-Fluoro-3-(3'-bromo-4-biphenylyl)-butan-3-ol;
1-Fluoro-3-(4'-bromo-4-biphenylyl)-butan-3-ol;
1-Fluoro-3-(2'-methyl-4-biphenylyl)-butan-3-ol;
1-Fluoro-3-(3'-methyl-4-biphenylyl)-butan-3-ol;
1-Fluoro-3-(4'-methyl-4-biphenylyl)-butan-3-ol;
1-Fluoro-3-(2',4'-difluoro-4-biphenylyl)-butan-3-ol;
1-Fluoro-3-(2'-methyl-4'-fluoro-4-biphenylyl)-butan-3-ol;
1-Fluoro-3-(2',4'-dichloro-4-biphenylyl)-butan-3-ol;
1-Fluoro-3-(4-phenoxy-phenyl)-butan-3-ol;
1-Fluoro-3-(4o-fluorophenoxy-phenyl)-butan-3-ol;
1-Fluoro-3-(4-m-fluorophenoxy-phenyl)-butan-3-ol;
1-Fluoro-3-(4-p-fluorophenoxy-phenyl)-butan-3-ol;
1-Fluoro-3-(4-o-chlorophenoxy-phenyl)-butan-3-ol;
1-Fluoro-3-(4-m-chlorophenoxy-phenyl)-butan-3-ol;
1-Fluoro-3-(4-p-chlorophenoxy-phenyl)-butan-3-ol;
1-Fluoro-3-(4-o-bromophenoxy-phenyl)-butan-3-ol;
1-Fluoro-3-(4-m-bromophenoxy-phenyl)-butan-3-ol;
1-Fluoro-3-(4p-bromophenoxy-phenyl)-butan-3-ol;
1-Fluoro-3-(4-o-tolyloxy-phenyl)-butan-3-ol;
1-Fluoro-3-(4-m-tolyloxy-phenyl)-butan-3-ol;
1-Fluoro-3-(4-p-tolyloxy-phenyl)-butan-3-ol;
1-Fluoro-3-[4-(2,4-difluorophenoxy)-phenyl]-butan-3-ol;
1-Fluoro-3-[4-(2-methyl-4-fluorophenoxy)-phenyl]-butan-3-ol; and
1-Fluoro-3-[4-(2,4-dichlorophenoxy)-phenyl]-butan-3-ol, are obtained from the corresponding 1-chloro compounds and KF.

EXAMPLE 129

A solution of 27.9 g. of 1-chloro-3-(4'-fluoro-4-biphenylyl)-butan-3-ol in 60 ml. of dimethylsulfoxide is added, at 80°, to a solution of 7.6 g. of NaCN in 100 ml. of dimethylsulfoxide. The mixture is warmed to 80°–90° for 6 hours, poured onto ice and worked up in the customary manner to give 1-cyano-3-(4'-fluoro-4-biphenylyl)-butan-3-ol, m.p. 118°–120°.

EXAMPLE 130–160

Analogously to Example 129,
1-Cyano-3-(4-biphenylyl)-butan-3-ol, m.p. 95°–96°;
1-Cyano-3-(2'-fluoro-4-biphenylyl)-butan-3-ol;
1-Cyano-3-(3'-fluoro-4-biphenylyl)-butan-3-ol;
1-Cyano-3-(2'-chloro-4-biphenylyl)-butan-3-ol;
1-Cyano-3-(3'-chloro-4-biphenylyl)-butan-3-ol;
1-Cyano-3-(4'-chloro-4-biphenylyl)-butan-3-ol; m.p. 136°–139°;
1-Cyano-3-(2'-bromo-4-biphenylyl)-butan-3-ol;
1-Cyano-3-(3'-bromo-4-biphenylyl)-butan-3-ol;
1-Cyano-3-(4'-bromo-4-biphenylyl)-butan-3-ol;
1-Cyano-3-(2'-methyl-4-biphenylyl)-butan-3-ol;
1-Cyano-3-(3'-methyl-4-biphenylyl)-butan-3-ol;
1-Cyano-3-(4'-methyl-4-biphenylyl)-butan-3-ol;
1-Cyano-3-(2',4'-difluoro-4-biphenylyl)-butan-3-ol;
1-Cyano-3-(2'-methyl-4'-fluoro-4-biphenylyl)-butan-3-ol;
1-Cyano-3-(2',4'-dichloro-4-biphenylyl)-butan-3-ol;
1-Cyano-3-(4-phenoxyphenyl)-butan-3-ol;
1-Cyano-3-(4-o-fluorophenoxy-phenyl)-butan-3-ol;
1-Cyano-3-(4-m-fluorophenoxy-phenyl)-butan-3-ol;
1-Cyano-3-(4-p-fluorophenoxy-phenyl)-butan-3-ol;
1-Cyano-3-(4-o-chlorophenoxy-phenyl)-butan-3-ol;
1-Cyano-3-(4-m-chlorophenoxy-phenyl)-butan-3-ol;
1-Cyano-3-(4-p-chlorophenoxy-phenyl)-butan-3-ol, m.p. 68° – 70°;
1-Cyano-3-(4-o-bromophenoxy-phenyl)-butan-3-ol;
1-Cyano-3-(4-m-bromophenoxy-phenyl)-butan-3-ol;
1-Cyano-3-(4-p-bromophenoxy-phenyl)-butan-3-ol;
1-Cyano-3-(4-o-tolyloxy-phenyl)-butan-3-ol;
1-Cyano-3-(4-m-tolyloxy-phenyl)-butan-3-ol;
1-Cyano-3-(4-p-tolyloxy-phenyl)-butan-3-ol;
1-Cyano-3-[4-(2,4-difluorophenoxy)-phenyl]-butan-3-ol;
1-Cyano-3-[4-(2-methyl-4-fluorophenoxy)-phenyl]-butan-3-ol; and
1-Cyano-3-[4-(2,4-dichlorophenoxy)-phenyl]-butan-3-ol, are obtained from the corresponding 1-chloro compounds and NaCN.

EXAMPLE 161

2.76 g. of 1-cyano-3-(4-phenoxy-phenyl)-butan-3-ol are dissolved in 20 ml. of acetic acid, a solution of 0.8 g. of chlorine in 20 ml. of acetic acid is added dropwise at 20° while stirring, the mixture is stirred for a further one hour and evaporated and the residue is worked up in the customary manner to give 1-cyano-3-(4-p-chlorophenoxy-phenyl)-butan-3-ol, m.p. 68° – 70°.

EXAMPLE 162

A solution of 2-fluoroethyl-lithium is prepared from 12.7 g. of 1-bromo-2-fluoroethane and 0.7 g. of Li in 200 ml. of THF and a solution of 21.4 g. of 4-p-fluorophenylacetophenone in 300 ml. of THF is added dropwise to this solution at 5° – 10°, under nitrogen. After stirring for one hour at about 20°, the alcoholate of the formula $p-F-C_6H_4-p-C_6H_4-C(OLi)$ $(CH_3)$ $(CH_2)_2F$, which has formed, is hydrolyzed by the dropwise addition of 50 ml. of water and then of 150 ml. of 3 N sulfuric acid, while stirring. Customary working up then gives 1-fluoro-3-(4'-fluoro-4-biphenylyl)-butan-3-ol, m.p. 90° – 92°.

EXAMPLE 163

A solution of 4'-fluoro-4-biphenylyl-magnesium bromide obtained from 2.51 g. of 4'-fluoro-4-bromo-biphenyl and 0.24 g. of magnesium in 100 ml. of ether is added dropwise, while stirring, at 20° to a solution of 0.9 g. of 1-fluorobutan-3-one in 40 ml. of ether, the mixture is stirred for a further 2 hours, the resulting alcoholate is decomposed with ice and saturated NH$_4$Cl solution and the mixture is worked up in the customary manner to give 1-fluoro-3-(4'-fluoro-4-biphenylyl)-butan-3-ol, m.p. 90° – 92°.

EXAMPLE 164

3 ml. of concentrated hydrochloric acid are added, at 0°, to 2.78 g. of 1-chloro-3-(4'-amino-4-biphenylyl)-butan-3-ol [which can be obtained by nitrating 1-chloro-3-(4-biphenylyl)-butan-3-ol and reducing the resulting 1-chloro-3-(4'-nitro-4-biphenylyl)-butan-3-ol] and a solution of 1.4 g. of NaNO$_2$ in 6 ml. of water is then added at 0°, while stirring. After adding a solution of 0.7 g. of boric acid in 1.5 g. of 60% hydrofluoric acid, the mixture is stirred for 40 minutes and filtered and the product is washed with water, methanol and ether and dried and the resulting diazonium fluoborate is heated to about 150° until decomposition is complete to give 1-chloro-3-(4'-fluoro-4-biphenylyl)-butan-3-ol, m.p. 78° – 79°.

EXAMPLE 165

2.78 g. of 1-chloro-3-(4'-amino-4-biphenylyl)-butan-3-ol are dissolved in 30 ml. of 10% hydrochloric acid, a solution of 0.7 g. of NaNO$_2$ in 2 ml. of water is added at 0°–5°, the resulting diazonium salt solution is added slowly dropwise to a hot solution of Cu$_2$Cl$_2$ (obtained by passing SO$_2$ into a hot solution of 2.1 g. of copper sulfate and 2.6 g. of NaCl in 13 ml. of water) and the mixture is heated to 90°–95° for a further 30 minutes, cooled and worked up in the customary manner to give 1-chloro-3-(4'-chloro-4-biphenylyl)-butan-3-ol, m.p. 98° – 100°.

EXAMPLE 166

Analogously to Example 164, 1-chloro-3-(4'-bromo-4-biphenylyl)-butan-3-ol is obtained with Cu$_2$Br$_2$.

EXAMPLE 167

Analogously to Example 164, 1-cyano-3-(4-p-chlorophenoxy-phenyl)-butan-3-ol, m.p. 68°–70°, is obtained from 1-cyano-3-(4-p-aminophenoxy-phenyl)-butan-3-ol [which can be obtained by nitrating 1-cyano-3-(4-phenoxy-phenyl)-butan-3-ol and subsequently reducing the reaction product].

EXAMPLE 168

2.6 g. of 3-(4'-fluoro-4-biphenylyl)-butane-1,3-diol [which can be obtained by a Reformatsky reaction of 4-p-fluorophenyl-acetophenone with ehtyl bromoacetate/zinc to give 3-(4'-fluoro-4-bipheylyl)-3-hydroxybutyric acid ethyl ester and reduction of the latter with LiAlH$_4$] and 5 ml. of SOCl$_2$ are stirred for 2 hours at 20° and the mixture is poured onto ice and worked up in the customary manner to give 1-chloro-3-(4'-fluoro-4-biphenylyl)-butan-3-ol, m.p. 78° – 79°.

EXAMPLE 169

A solution of 2.6 g. of 3-(4'-fluoro-4-biphenylyl)-1,3-butanediol in 10 ml. of pyridine is added dropwise, at −5°, while stirring, to a mixture of 1 g. of PBr$_3$, 1 ml. of pyridine and 3 ml. of benzene. The reaction mixture is then stirred for 24 hours at 20° and worked up in the customary manner to give 1-bromo-3-(4'-fluoro-4-biphenylyl)-butan-3-ol, m.p. 72° –74°.

EXAMPLE 170

4.14 g. of 3-(4'-fluoro-4-biphenylyl)-butane-1,3-diol-1-p-toluenesulfonate [which can be obtained by tosylation of the diol] and 2.9 g. of KF in 5 ml. of diethylene glycol are heated to 140° for 10 hours and the mixture is cooled and worked up in the customary manner to give 1-fluoro-3-(4'-fluoro-4-biphenylyl)-butan-3-ol, m.p. 90° –92°.

EXAMPLE 171

33.8 g. of 3-(4'-fluoro-4-biphenylyl)-butane-1,3-diol-1-methanesulfonate (which can be obtained from the diol and methanesulfonyl chloride in pyridine) are added to a solution of 10.3 g. of NaBr in 200 ml. of DMF and the mixture is left to stand for 100 hours at 25° and worked up in the customary manner to give 1-bromo-3-(4'-fluoro-4-biphenylyl)-butan-3-ol, m.p. 72° – 74°.

EXAMPLE 172

9.7 g. of KCN are dissolved in 150 ml. of DMF and a solution of 40 g. of 3-(4'-fluoro-4-biphenylyl)-butane-1,3-diol-1-benzenesulfonate in 150 ml. of DMF is added dropwise at 20°, while stirring. The mixture is heated to 80° for 6 hours, poured onto ice water and worked up in the customary manner to give 1-cyano-3-(4'-fluoro-4-biphenylyl)-butan-3-ol, m.p. 118° – 120°.

The examples which follow relate to pharmaceutical formulations which contain a phenylalkanol of Formula I.

EXAMPLE A: Tablets

A mixture of 1 kg. of 1-chloro-3-(4'-fluoro-4-biphenyl)-butan-3-ol, 4 kg. of lactose, 1.2 kg. of potato starch, 0.2 kg. of talc and 0.1 kg. of magnesium stearate is pressed to give tablets in the customary manner, in such a way that each tablet contains 100 mg. of the active compound.

EXAMPLE B: Dragees

Tablets are pressed analogously to Example A and subsequently are coated in the customary manner with a coating consisting of sucrose, potato starch, talc, tragacanth and a dyestuff.

EXAMPLE C: Capsules 5 kg. of 1-chloro-3-(4'-fluoro-4-biphenylyl)-butan-3-ol are filled into hard gelatine capsules in the customary manner so that each capsule contains 250 mg. of the active compound.

Tablets, dragees and capsules which contain one or more of the other active compounds of Formula I are obtainable analogously.

The preceding examples can be repeated with similar success by sustituting the generically or specifically described reactants and/or operating conditions of this invention for those used in the preceding examples.

From the foregoing description, one skilled in the art can easily ascertain the essential characteristics of this

What is claimed is:

1. A phenylalkanol of the formula

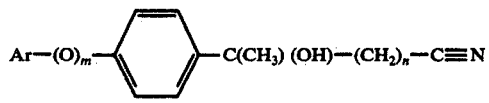

wherein Ar is phenyl or phenyl monosubstituted or disubstituted by F, Cl, Br or $CH_3$, $m$ is 0 or 1 and $n$ is 2 or 3.

2. A compound of claim 1 wherein Ar is phenyl, fluorophenyl, chlorophenyl, tolyl, difluorophenyl or fluorotolyl..

3. A compound of claim 1 wherein $n$ is 2.

4. A compound of claim 1 wherein $m$ is 0.

5. A compound of claim 4 wherein $n$ is 2.

6. A compound of claim 2 wherein wherein $m$ is 0 and $n$ is 2.

7. A compound of claim 1, 1-cyano-3-(4'-fluoro-4-biphenylyl)-butan-3-ol.

8. A compound of claim 1, 1-cyano-3-(4-p-chlorophenoxy-phenyl)-butan-3-ol.

9. A compound of claim 1, 1-cyano-3-(4-biphenylyl)-butan-3-ol.

10. A compound of claim 1, 1-cyano-3-(4'-chloro-4-biphenylyl)-butan-3-ol.

11. A pharmaceutical composition in unit dosage form comprising an antiinflammatorily effective amount per unit dosage of a compound of claim 1, in admixture with a pharmaceutically acceptable carrier.

12. A pharmaceutical composition of claim 11 adapted for oral ingestion.

13. A pharmaceutical composition according to claim 11 wherein m is 0.

14. A pharmaceutical composition according to claim 11 wherein the compound is 1-cyano-3-(4'-fluoro-4-biphenylyl)-butan-3-ol.

15. A pharmaceutical composition according to claim 11 wherein the compound is 1-cyano-3-(4'-chloro-4-biphenylyl)-butan-3-ol.

16. A method of treating inflammatory conditions which comprises administering systemically to the afflicted patient an antiinflammatorily effective amount of a compound of claim 1.

17. A method according to claim 16 wherein $m$ is 0.

18. A method according to claim 16 wherein the compound is 1-cyano-3-(4'-fluoro-4-biphenylyl)-butan-3-ol.

19. A method according to claim 16 wherein the compound is 1-cyano-3-(4'-chloro-4-biphenylyl)-butan-3-ol.

* * * * *